US009869064B2

(12) United States Patent
Akashi et al.

(10) Patent No.: US 9,869,064 B2
(45) Date of Patent: Jan. 16, 2018

(54) DEVICE FOR INSPECTING SHAPE OF ROAD TRAVEL SURFACE

(71) Applicant: WEST NIPPON EXPRESSWAY ENGINEERING SHIKOKU COMPANY LIMITED, Takamatsu-shi, Kagawa (JP)

(72) Inventors: Yukio Akashi, Takamatsu (JP); Kazuaki Hashimoto, Takamatsu (JP); Shogo Hayashi, Takamatsu (JP)

(73) Assignee: WEST NIPPON EXPRESSWAY ENGINEERING SHIKOKU COMPANY LIMITED, Takamatsu-shi, Kagawa (JP)

(*) Notice: Subject to any disclaimer, the term of this patent is extended or adjusted under 35 U.S.C. 154(b) by 151 days.

(21) Appl. No.: 14/785,233

(22) PCT Filed: Apr. 18, 2013

(86) PCT No.: PCT/JP2013/061504
§ 371 (c)(1),
(2) Date: Oct. 29, 2015

(87) PCT Pub. No.: WO2014/170989
PCT Pub. Date: Oct. 23, 2014

(65) Prior Publication Data
US 2016/0060824 A1 Mar. 3, 2016

(51) Int. Cl.
*E01C 23/01* (2006.01)
*G01B 11/30* (2006.01)
(Continued)

(52) U.S. Cl.
CPC ............ *E01C 23/01* (2013.01); *B60R 1/00* (2013.01); *G01B 11/30* (2013.01); *G01C 7/04* (2013.01);
(Continued)

(58) Field of Classification Search
CPC ........... E01C 23/01; B60R 1/00; G01B 11/30; G01B 7/04
See application file for complete search history.

(56) References Cited

U.S. PATENT DOCUMENTS 4,958,306 A * 9/1990 Powell .................. G01C 7/04
702/40
2010/0332127 A1* 12/2010 Imai ...................... B60W 30/12
701/532
(Continued)

FOREIGN PATENT DOCUMENTS

JP          9-14943  A     1/1997
JP          10-288516 A   10/1998
(Continued)

OTHER PUBLICATIONS

International Search Report of PCT/JP2013/061504 dated Aug. 20, 2013.

*Primary Examiner* — Mishawn Hunter
(74) *Attorney, Agent, or Firm* — Sughrue Mion, PLLC

(57) ABSTRACT

The present invention is capable of inspecting with high accuracy the shape of a road travel surface when travelling at a low speed, and even when acceleration, deceleration, or stoppages occur frequently, and generates a highly reproducible road surface longitudinal profile. A photograph is taken along the longitudinal direction of a travel path by a photography means in a light section method via a travel surface photography means (21). Corrected image information, in which a tilt in photographic image information has been corrected using inclination information, is generated on the basis of the photographic image information, the inclination information, and movement information via a road surface profile generation means (7), and thereafter the corrected image information is arranged using the movement information. Vertical motion information pertaining to
(Continued)

the travel surface photography means is specified from image contents of overlapped regions. One portion of the corrected image information is cut out, and extracted image information is generated. While the height of the corrected image is corrected using the vertical motion information from the corrected image information, the extracted image information is arranged sequentially, and connected, and the road surface profile is generated.

6 Claims, 12 Drawing Sheets

(51) Int. Cl.
  *G01C 7/04*   (2006.01)
  *B60R 1/00*   (2006.01)
  *G01N 33/42*   (2006.01)
  *H04N 7/18*   (2006.01)
  *G06T 3/40*   (2006.01)

(52) U.S. Cl.
  CPC ........... *G01N 33/42* (2013.01); *G06T 3/4038* (2013.01); *H04N 7/18* (2013.01); *B60R 2300/00* (2013.01); *G06T 2207/10028* (2013.01); *G06T 2210/61* (2013.01)

(56) References Cited

U.S. PATENT DOCUMENTS

| | | | |
|---|---|---|---|
| 2012/0263383 A1* | 10/2012 | Otuka | G06K 9/00798 382/195 |
| 2014/0118552 A1* | 5/2014 | Takahama | G06K 9/00798 348/148 |

FOREIGN PATENT DOCUMENTS

| | | |
|---|---|---|
| JP | 2000-088568 A | 3/2000 |
| JP | 2003-315001 A | 11/2003 |
| JP | 2005-315675 A | 11/2005 |
| JP | 2007-47137 A | 2/2007 |
| JP | 2008-82870 A | 10/2008 |
| JP | 5014464 * | 6/2012 |
| JP | 2012-173095 A | 9/2012 |

* cited by examiner

DEVICE FOR INSPECTING SHAPE OF ROAD TRAVEL SURFACE

CROSS REFERENCE TO RELATED APPLICATIONS

This application is a National Stage of International Application No. PCT/JP2013/061504 filed Apr. 18, 2013, the contents of which are incorporated herein by reference in its entirety.

TECHNICAL FIELD

The present invention relates to the device for inspecting the defect of the road travel surface.

BACKGROUND ARTS

On the travel surface of a paved road, such defects as a subsidence or deformation, a peeling off on the paved surface, a crushing of a paved surface are generated on the surface from such influencers as degradation over time, ground changes, excessive load, vibration, damages caused by falling objects.

Since such defects can signify serious destruction of a paved road, inhibit stability while traveling, and cause a noise incident to travel, it is imperative to detect early and repair these defects in maintenance management of the road.

The inspection of the travel surface of the paved road is largely grouped into the inspection method by photographing the road surface along the reference axis intersecting the travel direction of the vehicle and the inspection method performed along the reference axis along the travel direction of the vehicle.

Among the above inspection methods, the latter is required to analyze the flatness of the road travel surface.

As the prior arts used in such an inspection for the flatness of the road travel surface, Japanese Patent Application Laid-open No. 2003-315001, Japanese Patent Application No. 2005-315675, and Japanese Patent Application Laid-open No. 2012-173095 are already disclosed, for example.

In Japanese Patent Application Laid-open No. 2003-315001, the shape of the travel surface is inspected based on the displacement of the relative position of a plurality of rollers in contact with the travel surface, following on the road surface.

In Japanese Patent Application No. 2005-315675, the shape of the travel surface is inspected based on the acceleration or speed in the vertical direction of the suspension provided between the main body and the wheel of the vehicle.

These conventional arts include a contact-type device using rollers or wheels in contact with the travel surface, and the contact-style device bumps when the travel surface has a step and fails to inspect the shape of road surface with high-accuracy.

The Japanese Patent Application Laid-open No. 2012-173095 is a contactless conventional technology for inspecting the shape of the travel surface by using the accelerometer and a plurality of lasers.

When the travel surface has a step, even this contactless conventional technology fails to measure the step precisely.

Besides, in the above three kind of the prior arts, the inspection requires the vehicle speed to be maintained so as not to generate acceleration and deceleration exceeding the predetermined range.

Furthermore, in the above prior arts, no information capable of faithfully reproducing the unevenness of the shape of the travel surface can be acquired, no local displacement such as a step can be measured, scattering of aggregate on the surface of paved surface, etc. cannot be measured, and no clogging of spaces on the high-function pavement (a kind of permeable pavement) can be evaluated.

In addition, when the road travel surface is inclined or the vehicle gets on a step, the accompanying change of vehicle posture affects the acceleration in the measurement and causes the precise measurement to be inhibited.

By the way, IRI (traversing profile) measurement index is noted here as an estimation index for a road travel surface.

This IRI represents International roughness index, and is obtained by analyzing traversing profile data with IRI analysis program and calculated on the basis of information obtained from a laser displacement sensor, acceleration detector and speed detector, for example.

This IRI measurement is used for evaluating comfortableness of a traveling vehicle, and the evaluation using such an IRI measurement is regarded as globally common specifications.

At present, this evaluation system is used domestically in an expressway, etc.

However, the conventional IRI measurement requires a stable travel of the vehicle with the speed of 30-40 km/h or more, and thus, in the urban area where vehicles repeatedly stop, depart and perform acceleration and deceleration, and often travel with low speed, appropriate measurement results cannot be obtained due to the influence from the acceleration and deceleration, and any conditions such as measurement speed disperse the measurement accuracy and inhibit the measurement accuracy reference to be set.

Therefore, it is difficult to standardize IRI.

Besides, recently in the field of road travel surface state inspection, a light section method by photographing with the direction intersecting the travel direction as a reference axis is being developed.

Such a light section method is highly appropriate for inspecting the road travel surface state, whereas in the light section method performed by photographing the reference axis along the travel direction, a vehicle inclination state change or influence from acceleration and deceleration accompanied by the travel inhibits high-accuracy photographing, and no technique capable of effectively eliminating this problem has not yet been disclosed.

PRIOR ART DOCUMENTS

Patent Documents

Patent document 1: Japanese Patent Application Laid-open No. 2003-315001
Patent document 2: Japanese Patent Application No. 2005-315675
Patent document 3: Japanese Patent Application Laid-open No. 2012-173095

SUMMARY OF INVENTION

Problems to be Solved by the Invention

The present invention has been made for the purpose of solving the above problem. This invention aims at providing a device for inspecting the shape of road travel surface which can inspect the shape of road travel surface with high-accuracy even when a vehicle travels at a low speed or when acceleration, deceleration, or temporal stoppages occur frequently, can measure evenness and IRI with high reproducibility and precision, can precisely measure local displacement such as a step, can faithfully reproduce the fine unevenness of the road surface, can measure scattering of aggregate, etc. on the surface of paved surface, can evaluate clogging of spaces on the high-function pavement such as permeable pavement, and can faithfully reproduce the three-dimensional shape of the road travel surface by acquiring two lines of profiles along the travel direction of the road travel surface and then combining the profiles with the data along the direction intersecting the travel direction on the road travel surface.

Means to Solve the Problem

In order to solve the above problem, the device in the first invention in the present invention for inspecting the shape of road surface is characterized in that the device installed in a vehicle, for photographing road travel surface while the vehicle travels and inspecting a shape of the road travel surface based on photographic information obtained by the photographing, comprising travel surface illumination means for emitting a light beam to the road travel surface along a travel surface photography axis set parallel to a travel direction of the vehicle, travel surface photography means installed in the vehicle at a predetermined reference angle for acquiring information necessary for a light section method by sequentially photographing from an oblique direction, with a predetermined photography range set as a unit, the travel surface photography axis in regions to which the light beam is emitted by the travel surface illumination means as a plurality of units of photography ranges of photographic images, and acquiring photographic image information, inclination information generation means for acquiring inclination information which shows inclination state of the travel surface photography means, movement information acquisition means for acquiring travel distance information of the vehicle, and road surface profile generation means for generating a road surface profile by generating corrected image information in which a tilt in the photographic image information has been corrected by using the inclination information, on the basis of the photographic imager information, the inclination information, and the movement information, then arranging the corrected image information by using the movement information, specifying vertical movement information pertaining to the travel surface photography means from image contents of overlapped regions, generating extracted image information by partially cutting out the corrected image information and, while correcting height of the corrected image by using the vertical movement information from the corrected image information, sequentially arranging and connecting the extracted image information.

Also, the device for inspecting the shape of the road travel surface in the second invention is, in the first invention, characterized in that the road surface profile generation means comprises extracted image information generation means for segmenting the photographic image to be cut out into a front region and a rear region in the travel direction on the basis of a central axis orthogonal to a travel surface reference axis, as the rear region, in a series of photographic processes, setting a width corresponding to a length which is half a movement distance specified based on the travel distance information is set, the travel distance information being to the photography position of the photographic image to be cut out from the photographic image initially photographed in a case where no photographic image has been cut out among the photographic images photographed prior to the photographic image to be cut out, and from the photography position of the photographic image which has been cut out immediately before the photographic image to be cut out in a case where any photographic images have been cut out among the photographic images photographed prior to the photographic image to be cut out, as the front region, setting a width corresponding to the length which is half the movement distance specified based on the travel distance information from the photography position of the photographic image to be cut out to the photography position of the photographic image to be cut out immediately after the photographic image to be cut out, and generating the extracted image information by cutting out an extracted region formed of the front region and the rear region sandwiching the central axis of the photographic image to be cut out.

Also, the device for inspecting the shape of the road travel surface in the third invention is, in the second invention, characterized in that the road surface profile generation means further comprises basic information generation means for generating basic information in which all photographic image information and movement distance information at photography timing of each photographic image information are associated, photographic image information selection means for specifying from the basic information relative position of the photographic image generated by the photographic image information in each unit, sequentially specifying, in the photographic images in each unit, the photographic images in which an edge region of the travel surface photography axis included in each photographic image overlaps the edge region of the other photographic image within a predetermined range, and selecting the photographic image information corresponding to the specified photographic images, movement distance information generation means for generating movement distance information of the travel surface photography means at the photography timing of the each selected photographic image, based on the movement distance information associated with the selected photographic image information, corrected image information generation means for generating the corrected image information in the units respectively corresponding to the selected image information in each unit by correcting the selected photography image information into the corrected image information photographied from a predetermined and specific angle by the use of the inclination information of the travel surface photography means associated with the photographic image information, the vertical movement information generation means for generating the relative vertical movement information of the cameras by comparing the overlapped regions of the images included in the neighboring corrected image information in the corrected image information in each unit, calculating the relative height displacement of cameras which have photographied the corrected image information from the distance of the positions of the light beam image included in the corrected image information, and the extracted image information connection means for generating the road surface profile by sequentially arranging and connecting each extracted image information while reflecting the vertical movement information and correcting the displacement in the vertical direction, the extracted image information generation means generating the extracted image information from the corrected images generated from the corrected image information corrected by the corrected image information generation means.

Also, the device for inspecting the shape of the road travel surface in the fourth invention is, in either of the first-third inventions, characterized in that the travel surface photography means measures the height of the travel surface photography means to the road travel surface in addition to photographing the road travel surface, the travel surface photography means comprising auxiliary travel surface illumination means for emitting the light beam to the road travel surface along a travel surface auxiliary photography axis set parallel to the travel direction of the vehicle, and auxiliary travel surface photography means installed in the vehicle at the predetermined reference angle, for acquiring auxiliary photographic image information by sequentially photographing the travel surface auxiliary photography axis in the region where the auxiliary travel surface illumination means emits the light beam, from the oblique direction to the road travel surface with the predetermined photography range set as a unit while synchronizing the auxiliary photographic images in the plurality of units of photography ranges with the photography timing of the travel surface photography means, and acquiring information necessary for light section means from the road travel surface at the photography timing of the auxiliary travel surface photography means, the auxiliary travel surface photography means at least measuring auxiliary height of auxiliary travel surface to the road travel surface, inclination information generation means using information of height of the travel surface photography means, auxiliary height of the auxiliary travel surface photography means, and the distance between the travel surface photography means and the auxiliary travel surface photography means, calculating a posture change angle between the travel surface photography means and the auxiliary travel surface photography means, generating the inclination information of the vehicle while using the posture change angle as the inclination information of the vehicle, and using the inclination information of the vehicle as the inclination information of the travel surface photography means.

Also, the device for inspecting the shape of the road travel surface in the fifth invention is, in the fourth invention, characterized in that a posture change angle θ is obtained by the formula shown below in a case where, among the photographic images selected by the photographic image information selection means, two sequential photographic images include an identical reference point P 1, and, in the two photographic images, height of the travel surface photography means of an antecedently photograpied photographic image is defined as H 1, and height of the travel surface photography means of a subsequently photograpied photographic image is defined as H 1', two sequential auxiliary photographic images photographied in synchronization with the photography timing of the photographic images photographied by the auxiliary travel surface photography means and selected by the photographic image information selection means include an identical reference point P 2 and, in the two auxiliary photographic images, auxiliary height of auxiliary travel surface photography means of an antecedently photograpied auxiliary photographic image is defined as H 2, and auxiliary height of the auxiliary travel surface photography means of a subsequently photograpied auxiliary photographic image is defined as H 2', and distance between the travel surface photography means and the auxiliary travel surface photography means is defined as L.

$$\text{posture change angle } \theta = \text{Atan}\frac{(H1' - H2') - (H1 - H2)}{L} \quad \text{[Formula 1]}$$

Also, the device for inspecting the shape of the road travel surface in the sixth invention is, in the first or second invention, characterized in that the inclination information generation means is a gyro system, and the road surface profile generation means further comprises the basic information generation means for specifying, for all the photographic image information, the inclination information at the photography timing of the photographic image information, specifying movement information corresponding to the photography timing and generating the basic information in which the inclination information and the movement information are associated with the photographic image information, the photographic image information selection means for calculating from the association of the photographic image information and the movement information the relative position of the photographic image generated by the photographic image information in each unit, sequentially specifying the photographic images in which the edge region of the travel surface photography axis included in each photographic image overlaps the edge region of the other photographic image within the predetermined range, and selecting the photographic image information generating the specified photographic images, the movement distance information generation means for generating the movement distance information of the cameras at the photography timing of each photographic image, based on the movement distance information associated with selected photographic image information, the corrected image information generation means for generating the corrected image information in the units respectively corresponding to the selected image information in each unit, by correcting the selected photography image information into the corrected image information photographied from the reference angle based on the angle information of the cameras associated with the photography image information by the use of relative photography angle information on the basis of the reference angle of the cameras, the vertical movement information generation means for generating the relative vertical movement information of the cameras by comparing the overlapped regions of the images included in the neighboring corrected image information in the corrected image information in each unit, calculating the relative height displacement of cameras which have photographied the corrected image information from the distance of the positions of the light beam image included in the corrected image information, and the extracted image information connection means for generating the road surface profile by sequentially arranging and connecting each extracted image information while reflecting the vertical movement information and correcting the displacement in the vertical direction.

Effect of the Invention

In the present invention, the speed and acceleration of the vehicle during the photographing do not affect the finally generated road surface profile, therefore, the surface shape of the road travel surface can be reproduced with high-accuracy not only on the express way but also on the road such as in the urban area where acceleration, deceleration, or temporal stoppages occur frequently and the vehicle often travels at a low speed.

Besides, the high-accuracy measurement of the road surface shape enables evenness and IRI to be inspected with high-accuracy by the use of the generated road surface profile.

In addition, no dumping of the vehicle such as leaping up and sinking on the step reflected on the road surface profile achieves the high-accuracy measurement of the road surface shape and enables the local displacement such as a step to be precisely measured.

Also, the characteristic of the light section method enables the fine unevenness of the road surface to be faithfully reproduced on the road surface profile, and thus, enables scattering of aggregate, etc. on the road travel surface, namely on the surface of paved surface to be measured and thereby the surface state of the high-function pavement to be inspected quite favorably.

Also, when the surface of the high-function pavement is inspected, the clogging of spaces can be evaluated, as well.

Also, by acquiring two lines of road surface profiles along the travel direction of the road travel surface and then combining the profiles with the data along the direction intersecting the travel direction on the road travel surface, the three-dimensional shape of the road travel surface can be faithfully reproduced and the shape of the road travel surface can be inspected more precisely.

To be specific, in the first invention, the road surface profile is generated by partially cutting out, arranging, and combining each photographic information photographied by the light section method and corrected on the basis of the camera inclination information, and thus, the generated road surface profile can reproduce the surface shape of the actual road travel surface with high-accuracy.

In the second invention, the range corresponding to the travel speed of the vehicle can be cut from the photographic images as the extracted region, namely as the extracted images, and by sequentially arranging and connecting the region, the road surface profile which reproduces with high accuracy the inspected road travel surface can be generated regardless of the travel speed or temporal stoppages of the vehicle.

In the third invention, the scales of each photographic image information which vary in the axis direction along the travel direction according to the photography angle can be unified to be specific by correcting the photographic images according to the photography angle of the camera at the time when the selected photographic image information is acquired, and thereby the overlapped regions in each selected photographic image information can be compared, the vertical movement information of the camera corresponding to each of these photographic image information can be generated, and finally, the precise road surface profile can be generated by connecting the extracted image information while correcting the displacement in the vertical direction.

In the fourth and fifth inventions, the use of one set of the two light section units enables the height from the road travel surface in the front and the rear of the vehicle to be calculated, thereby the precise vehicle inclination information can be generated without being affected by the acceleration/deceleration or the floating/sinking of the vehicle at the time when the vehicle passes a step, etc., and as a result, the corrected image information can be generated precisely.

In the sixth invention, the photographic image information based on the light section method enables the precise road surface profile to be generated.

EMBODIMENTS FOR IMPLEMENTING THE INVENTION

In the present invention, the vertical section profile information of the road travel surface is generated by the light section method, wherein a three-dimensional camera is used, for example, as the travel surface photography means, the slit laser beam emitted from the travel surface illumination means along the travel surface photography axis set parallel to the travel direction on the road travel surface is photographed, and thereby the shape of the road travel surface is inspected.

The prevent invention is explained in detail based on the embodiments hereinafter.

Embodiment 1

Figure 1:
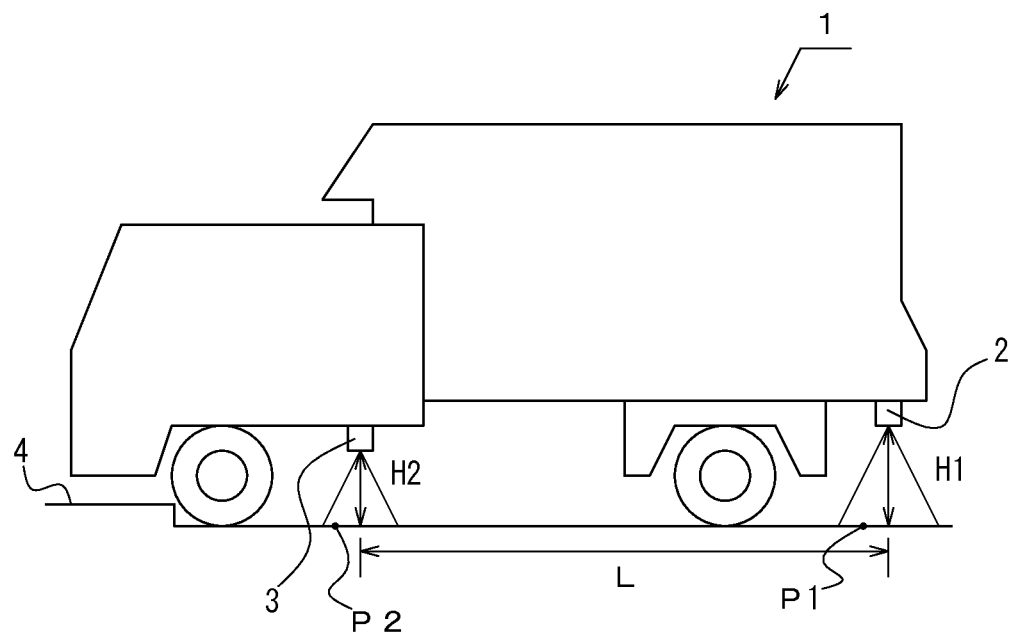
FIG. 1 is a conceptual diagram showing the photographing state in Embodiment 1 of the vehicle mounted with the device for inspecting the shape of the road travel surface in the present invention.
Figure 2:
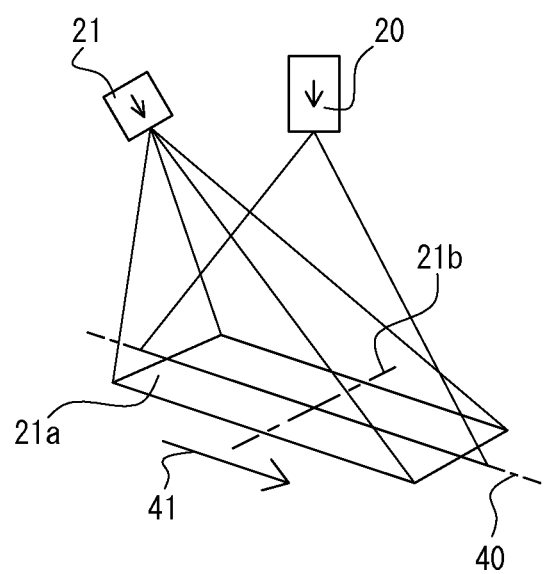
FIG. 2 is a conceptual diagram showing the basic structure of the light-section unit 2 shown in FIG. 1.
Figure 3:
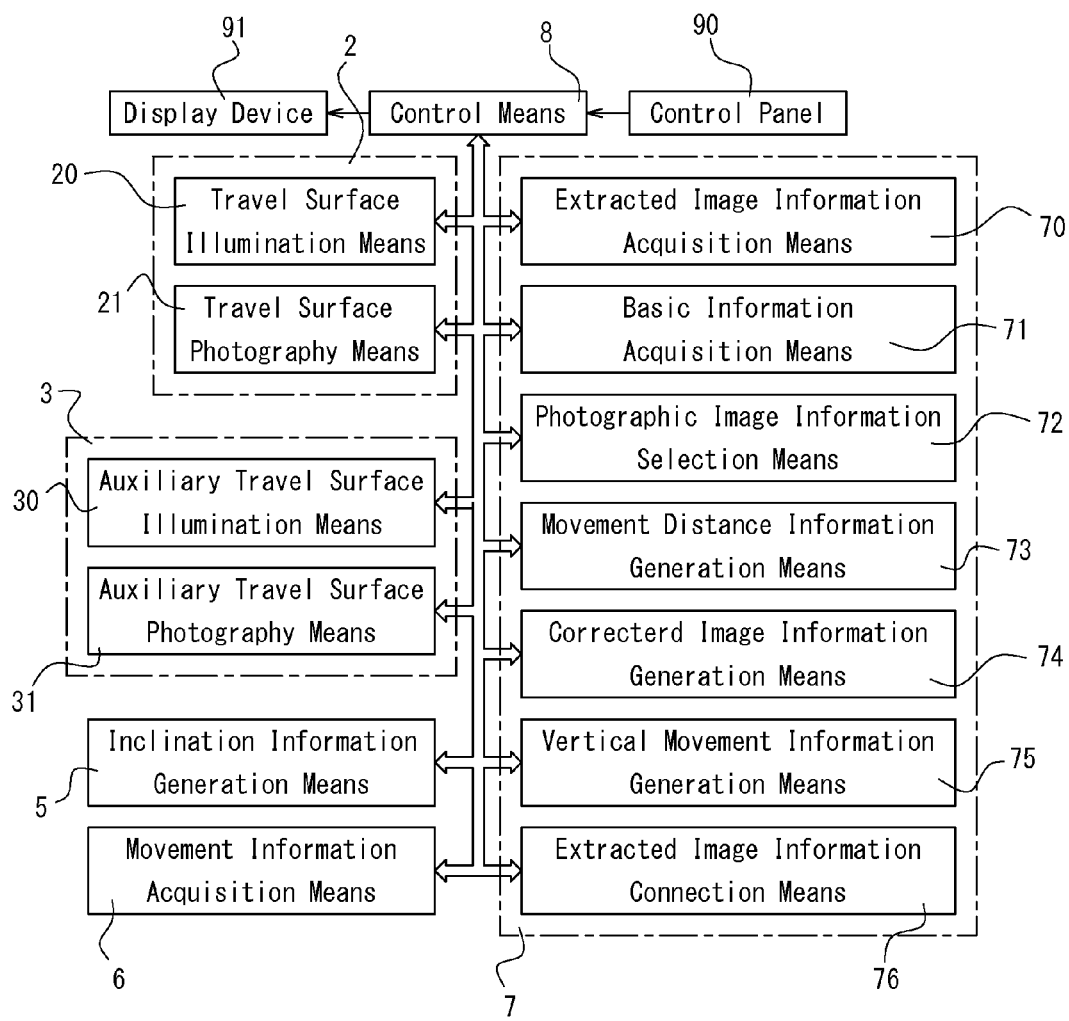
FIG. 3 is a block diagram showing the system configuration of the device shown in FIG. 1.
Figure 4:
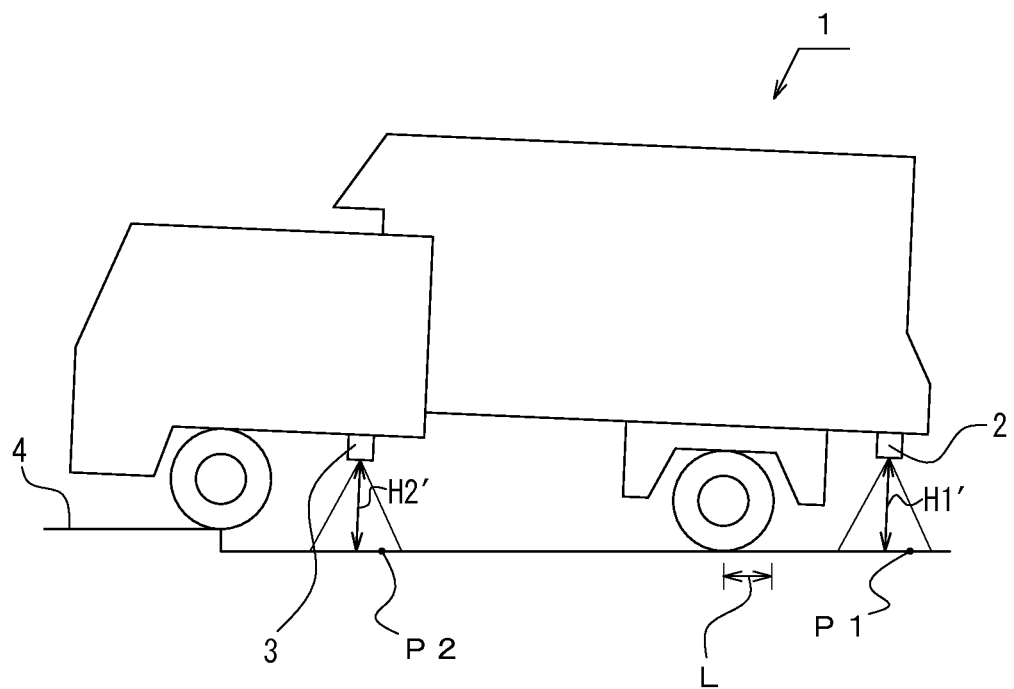
FIG. 4 is a conceptual diagram showing the photographing state of the vehicle over roads shown in FIG. 1.
Figure 5:
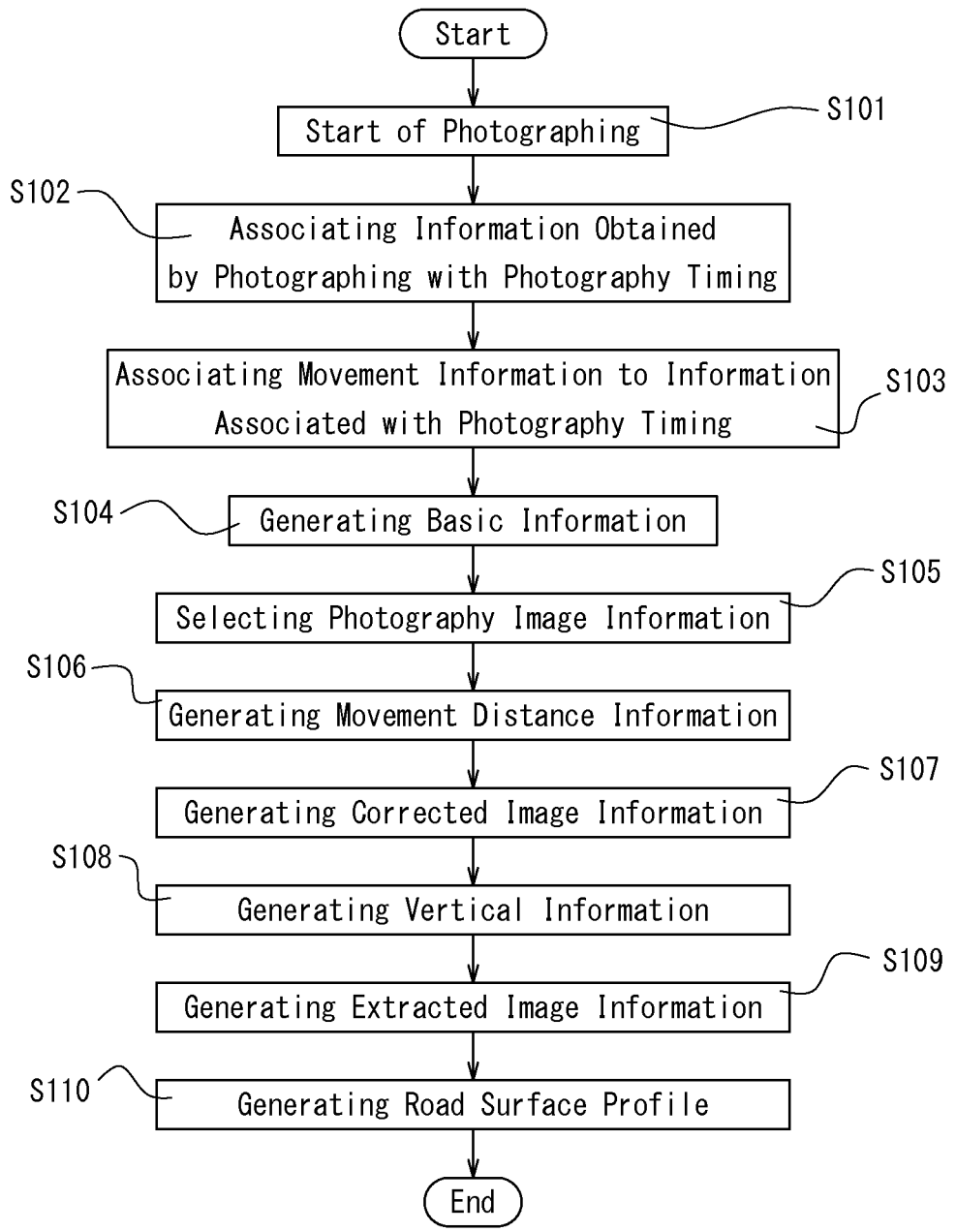
FIG. 5 is a flow chart showing an example of process for generating the road surface profile in Embodiment 1.
Figure 6:
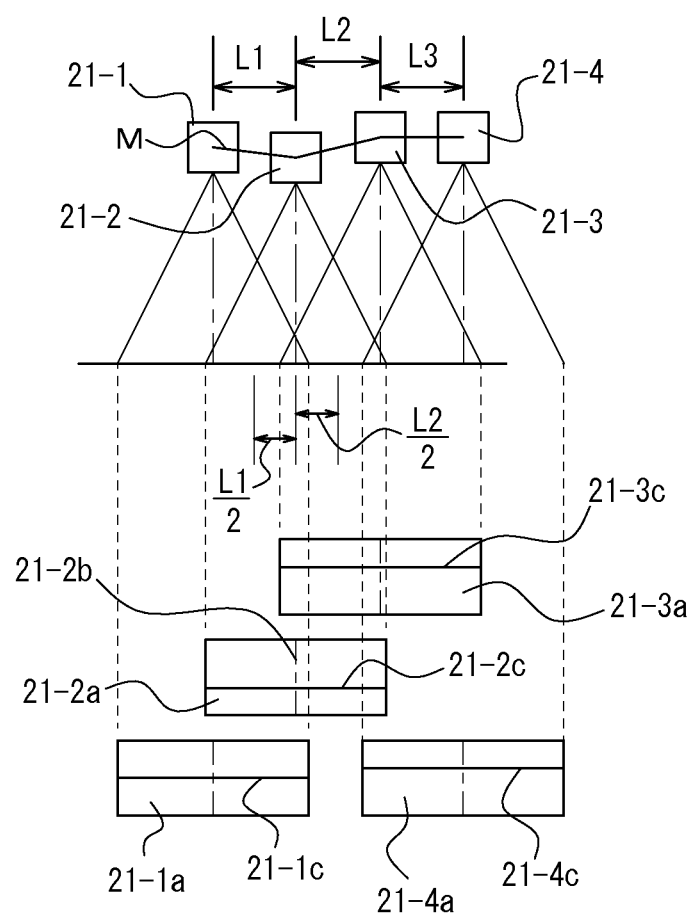
FIG. 6 is an explanation drawing showing the state of the photographic image acquired in Embodiment 1.
Figure 7:
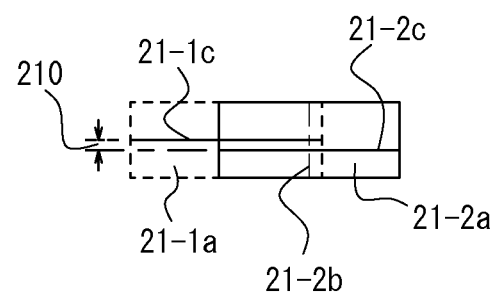
FIG. 7 is a plan view showing how the photographic images are overlapped in Embodiment 1.
Figure 8:
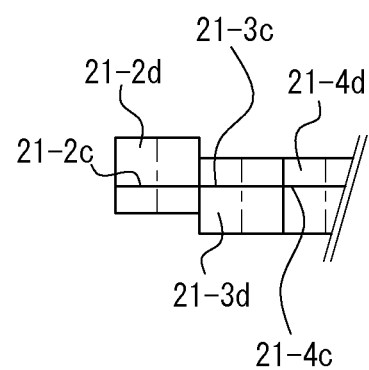
FIG. 8 is a plan view showing how the extracted images are connected in Embodiment 1.
Figure 9:
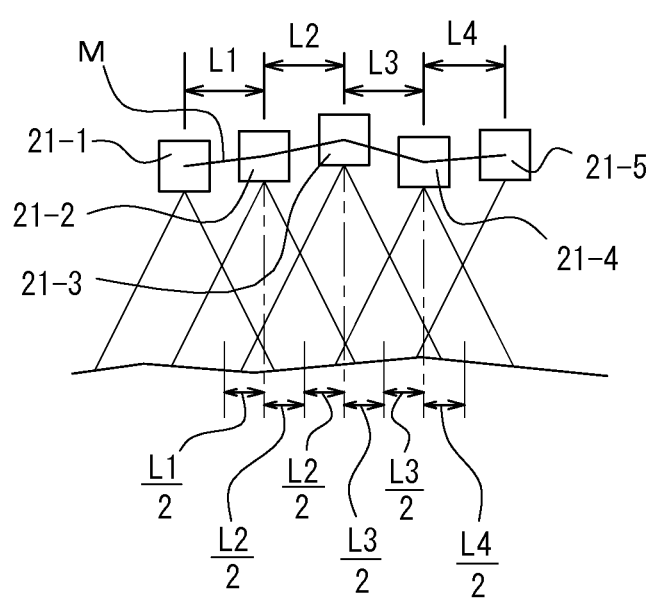
FIG. 9 is an explanation drawing showing how the movement distance and the extracted regions are related to each other in Embodiment 1.
Figure 12:
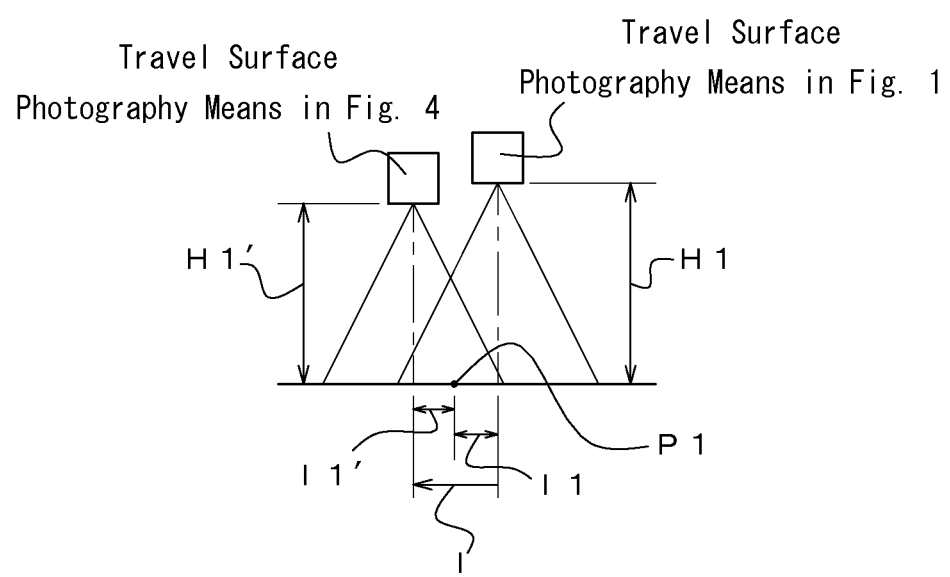
FIG. 12 is a conceptual diagram showing the relative position of the travel surface photography means in FIG. 1 and FIG. 4.

FIG. 1 is a conceptual diagram of the Embodiment 1 of the vehicle mounted with the device for inspecting the shape of the road travel surface in the present invention. FIG. 2 is a conceptual diagram showing the basic structure of the light-section unit 2 shown in FIG. 1. FIG. 3 is a block diagram showing the system configuration of the device shown in FIG. 1. FIG. 4 is a conceptual diagram showing the photographing state of the vehicle over roads shown in FIG. 1. FIG. 5 is a flow chart showing an example of process for generating the road surface profile in Embodiment 1. FIG. 6 is an explanation drawing showing the state of the photographic image acquired in Embodiment 1. FIG. 7 is a plan view showing how the photographic images are overlapped in Embodiment 1. FIG. 8 is a plan view showing how the extracted images are connected in Embodiment 1. FIG. 9 is an explanation drawing showing how the movement distance and the extracted regions are related to each other in Embodiment 1. FIG. 12 is a conceptual diagram showing the relative position of the travel surface photography means in FIG. 1 and in FIG. 4.

At first, FIG. 1 and FIG. 2 are explained. The reference numerals in the drawings respectively indicate as shown below. 1: vehicle mounted with the device for inspecting the shape of the road travel surface in the present invention (Embodiment 1), 2: light section unit provided backward of the rear wheel of the vehicle 1, 20: travel surface illumination means provided in the light section unit 2, 21: travel surface photography means provided in the light section unit 2, 21 *a*: photography range of travel surface photography means 21, 21 *b*: central axis of travel surface photography means 21, 3: auxiliary light section unit provided behind the front wheel of the vehicle 1, 4: road travel surface, 40: travel surface photography axis set on the road travel surface 4, 41: travel direction of the vehicle 1.

The vehicle 1 is a work vehicle with a base of work track used for road maintenance work, for example.

The light section unit 2 is provided at the rear part of the bottom surface of the vehicle 1 so as to face the road travel surface 4.

The light section unit 2 comprises the travel surface illumination means 20 and the travel surface photography means 21.

The travel surface illumination means 20 can emit the slit laser beam against the road travel surface 4 vertically or approximately vertically to the travel surface photography axis 40 set parallel to the travel direction 41 of the vehicle 1.

The travel surface photography means 21 photographies the travel surface photography axis 40 in the region which the travel surface illumination means 20 emits the light beam from the oblique direction against the road travel surface 4 as the predetermined photography range 21*a*, and is a camera including a 3D camera, for example.

In the photography range 21 *a*, the central axis 21 *b* is set at the center of the photography range 21 *a* and orthogonal to the travel surface photography axis 40.

The auxiliary light section unit 3 is provided behind the front wheel on the bottom surface of the vehicle 1 so as to face the road travel surface 4.

This auxiliary light section unit 3 comprises the auxiliary travel surface illumination means 30 and the auxiliary travel surface photography means 31 as shown in FIG. 3, as well as the light section unit 2 which comprises the travel surface illumination means 20 and the travel surface photography means 21, and the auxiliary travel surface photography axis (not shown) overlapping the extended travel surface photography axis 40 set in the light section unit 2 is set in the auxiliary light section unit 3.

Next, the system configuration of the device shown in FIG. 1 is explained based on FIG. 3. It should be noted that the same reference numerals are added in the overlapping configurations in FIG. 1 and FIG. 2, and the overlapping explanations are omitted.

In FIG. 3, the reference numerals respectively indicate as shown below. 8: control means for controlling the operation of the device in FIG. 1, 3: auxiliary light section unit provided behind the front wheel of the vehicle 1, 30: auxiliary travel surface illumination means provided in the auxiliary light section unit 3, 31: auxiliary travel surface photography means provided in the auxiliary light section unit 3, 5: inclination information generation means controlled by the control means 8, 6: movement information acquisition means controlled by the control means 8, 7: road surface profile generation means controlled by the control means 8, 70: extracted image information generation means provided in the road surface profile generation means 7, 71: basic information generation means provided in the road surface profile generation means 7, 72: photographic image information selection means provided in the road surface profile generation means 7, 73: movement distance information generation means provided in the road surface profile generation means 7, 74: corrected image information generation means provided in the road surface profile generation means 7, 75: vertical movement information generation means provided in the road surface profile generation means 7, 76: extracted image information connection means provided in the road surface profile generation means 7, 90: control panel for an operator, etc., to operate and input a signal for operating the control means 8, 91: display device for displaying at least the generated road surface profile.

Besides, in addition to the above configurations, an output device such as a printing device may be provided if necessary, and the input operation by the operator or the display of the road surface profile may be performed via the connected mobile terminal.

The control means 8 allows each component constituting the device in the present invention to be operated according to the predetermined program to generate the road surface profile.

Therefore, the each component is operated as explained below according to the direction signal from the control means 8.

The travel surface illumination means 20 in the light section unit 2 emits the light beam along the travel surface photography axis.

The travel surface photography means 21 in the light section unit 2 photographies the predetermined photography range 21 *a* periodically and sequentially, and sequentially photographies the photographic images of a plurality units of photography ranges setting the photography range photograpied in one photography session as one unit, to acquire the photographic image information, and also, measures the height of the travel surface photography means 21 to the road travel surface at the time when each photographic image information is photographed from the information obtained from the photographing to acquire the height information corresponding to each photographic image information.

Also, the synchronized information showing each photography timing is associated with the each photographic image information obtained by the travel surface photography means 21.

The auxiliary travel surface illumination means 30 in the auxiliary light section unit 3 emits the light beam along the auxiliary travel surface photography axis.

The auxiliary travel surface photography means 31 in the auxiliary light section unit 3 photographies while being synchronized with the photography timing of the travel surface photography means 21 of the light section unit 2, and measures the auxiliary height of the auxiliary travel surface photography means 31 to the road travel surface at the time of each photographing from the information obtained by the photographing to acquire the auxiliary height information corresponding to each photography timing.

Also, the synchronized information showing each photography timing is associated with the each auxiliary height information obtained by the auxiliary travel surface photography means 31.

The inclination information generation means 5 calculates the posture change angle of the vehicle 1 based on the height information obtained by the travel surface photography means 21 and the auxiliary height information obtained by the auxiliary travel surface photography means 31 to generate the inclination information of the vehicle by using the obtained posture change angle as the inclination information of the vehicle.

The method for calculating the posture change angle is explained below based on FIGS. 1, 4 and 12.

In these drawings, the height of the travel surface photography means 21 at the time when the photographing is performed in the traveling vehicle 1 in FIG. 1 is defined as H 1, and the height of the travel surface photography means 21 in the traveling (FIG. 4) vehicle at the time when the photographic image to be selected by the below shown photographic image information selection means following the photographic image in FIG. 1 is photographed is defined as H 1'.

Also, the height of the auxiliary travel surface photography means at the photography timing in FIG. 1 is defined as H 2, and the height of the auxiliary travel surface photography means at the photography timing in FIG. 2 is defined as H 2'.

Also, the distance between the travel surface photography means and the auxiliary travel surface photography means is defined as L.

It is noted that in FIGS. 1 and 4, each height and distance is shown on the basis of the light section unit 2 or the auxiliary light section unit 3 for convenience sake, but in reality, is supposed to be shown on the basis of each photography means provided in each unit.

The photography range of the travel surface photography means in FIG. 1 includes the position P 1, and the photographic image selection is set so that P 1 is also included in the photography range of the travel surface photography means in FIG. 4.

Also similarly, the photography range of the auxiliary travel surface photography means in FIG. 1 includes the position P 2, and P 2 is also included in the photography range of the auxiliary travel surface photography means in FIG. 4.

Also, the movement amount I from FIG. 1 to FIG. 4 can be acquired by the movement information acquisition means 6 mentioned below.

Here, in order to clarify the above state, it is explained how the relative position of the travel surface photography means is related between in FIG. 1 and in FIG. 4 on the basis of FIG. 12.

It should be noted that in FIG. 12 the photography direction of each travel surface photography means is corrected to be vertical to the travel surface for convenience sake.

In FIG. 12 the position P1 is a point commonly set and the relative positions of the travel surface photography means positioned in the different timings are specified on the basis of the position P1.

And, FIG. 12 shows how the relative positions between the reference axes in the photographing by the travel surface photography means in the timings in FIG. 1 and in FIG. 4 and the position P 1 are related.

In FIG. 12, when the interval between the reference axes in the photographing by the travel surface photography means in FIG. 1 and in FIG. 4 is defined as the movement amount I, the below relationship is formed.

$$I = I1 + I1'$$

$$I1' = I - I1$$

In the above formulas, the movement amount I represents the movement distance of the vehicle 1 from the photography timing in FIG. 1 to the photography timing in FIG. 2, obtained by the measurement of a distance meter such as the movement information acquisition means 6, for example.

And, this movement amount I is set so that the photographic images are selected in the interval set so as to be about half the measurement width of the light section or smaller, and more preferably, the measurement width of the light section and the vehicle speed are adjusted so that the photographing is performed within the above interval.

Also, I 1 is a fixed value set in advance, and to be specific, is recommended to be set so as to be about a quarter of the measurement width of the light section.

Accordingly, I 1' varies according to the size of the movement amount I.

It should be noted that, although FIG. 12 seems to show that the position P 1 matches the boundary of I1 and I 1', the relative position of the two varies according to how I 1 is set.

It should be noted that the relative relationship to the position P 1 in the above travel surface photography means is similar to the relative relationship to the position P 2 in the auxiliary travel surface photography means.

In this embodiment, the height H 1 and H 1' respectively in FIG. 1 and FIG. 4 are set on the basis of the common position P 1 and the height H 2 and H 2' are set on the basis of the common position P 2, and thus the inclination state of the vehicle 1, namely the posture change of the vehicle can be measured.

Since the movement amount I varies according to the travel speed of the vehicle 1, the measurement by the travel surface photography means and the auxiliary travel surface photography means via the light section method is essential.

Based on the above, the posture change angle θ is calculated by the formula shown below.

$$\text{posture change angle } \theta = \operatorname{Atan}\frac{(H1' - H2') - (H1 - H2)}{L} \quad \text{[Formula 1]}$$

The movement information acquisition means 6 associates the travel distance information obtained by measuring the travel distance obtained by the travel of the vehicle 1 with the photography timing of the travel surface photography means 21 as the movement information of the travel surface photography means 21, thereby acquires the movement information.

The road surface profile generation means 7 comprises the extracted image information generation means 70, the basic information generation means 71, the photographic image information selection means 72, the movement distance information generation means 73, the corrected image information generation means 74, the vertical movement information generation means 75, and the extracted image information connection means 76.

The extracted image information generation means 70 generates the extracted image information from one unit of photographic images as mentioned below, the road surface profile being generated from the extracted image information.

At first, the photographic images selected by the photographic image information selection means 72, namely the photographic images to be cut out, is segmented into the front region and the rear region in the travel direction on the basis of the central axis 21 *b* (FIG. 2) orthogonal to the travel surface reference axis.

Next, as the rear region, in a series of photographic processes, the width corresponding to the length which is half the movement distance specified based on the travel distance information generated by the movement distance information generation means 73 is set, the travel distance information being to the photography position of the photographic image to be cut out from the photographic image initially photographed in a case where no photographic image has been cut out among the photographic images photographed prior to the photographic image to be cut out, and from the photography position of the photographic image which has been cut out immediately before the photographic image to be cut out in a case where any photographic images have been cut out among the photographic images photographed prior to the photographic image to be cut out.

Also, as the front region, the width corresponding to the length which is half the movement distance specified based on the movement information from the photography position of the photographic image to be cut out to the photography position of the photographic image to be cut out immediately after the photographic image to be cut out is set.

Next, the extracted image information is generated by cutting out from the photographic image to be cut out the extracted region formed of the front region and the rear region sandwiching the central axis of the photographic image to be cut out.

The basic information generation means 71 generates the basic information in which all photographic image information acquired via the travel surface photography means 21 and the movement distance information at the photography timing of each photographic image information are associated.

The photographic image information selection means 72 specifies from the basic information the relative position of the photographic image generated by the photographic image information in each unit, sequentially specifies, in the photographic images in each unit, the photographic images in which the edge region of the travel surface photography axis included in each photographic image overlaps the edge region of the other photographic image within the predetermined range, and selects the photographic image information corresponding to the specified photographic images.

The movement distance information generation means 73 is based on the movement distance information associated with the selected photographic image information, and generates the movement distance information of the travel surface photography means with the photography timing used as a unit, based on the distances between the relative positions of the travel surface photography means at the photography timing of the each selected photographic image information.

The corrected image information generation means 74 generates the corrected image information in the units respectively corresponding to the selected image information in each unit, by correcting the photographic image information selected by the photographic image information selection means 72 into the corrected image information photographied from the predetermined and specific angle by the use of the inclination information of the travel surface photography means 21 associated with the photographic image information.

To be specific, the photography angle of the travel surface photography means at the time when the photographic image information is acquired in the state shown in FIG. 1, for example, is used as the reference angle.

In contrast, the relative photography angle of the travel surface photography means in the state shown in FIG. 4 is inclined by a certain angle to the reference angle.

Therefore, the scale of the photographic image obtained by the travel surface photography means is increased along the travel direction more in FIG. 4 than in FIG. 1, and the image is distorted.

Accordingly, each photographic image is corrected into the image photographied from the reference angle by correcting the photographic image information based on the inclination information of the travel surface photography means 21.

As a result, the inclination of the each photographic image is corrected.

The vertical movement information generation means 75 compares the overlapped regions of the images included in the neighboring corrected image information in the corrected image information in each unit, calculates the relative height displacement of the travel surface photography means 21 which have photographed the corrected image information, from the distance of the positions of the light beam image included in the corrected image information, and thereby, generates the relative vertical movement information of the travel surface photography means 21.

Here, "neighboring corrected image information" indicates the corrected image information which are lined while being partially overlapped, when each corrected image information is sequentially arranged in order of the movement distance in reference to the movement distance information of the basic information, based on the basic information corresponding to the photographic image information as the material of each corrected image information.

The overlapped parts of the neighboring corrected image information include the light beam images of which the shapes are similar to each other, and the inclination of the travel surface photography means changes the distance between the travel surface photography means 21 and the central axis 21 *b*.

Therefore, analyzing an specifying the difference of the light beam images enables the difference between the travel surface photography means 21 and the central axis 21 *b*, namely the height of the travel surface photography means 21 to the road travel surface to be specified, and the relative vertical movement information of the travel surface photography means 21 to be generated.

The extracted image information connection means 76 sequentially arrange and connect each extracted image information while correcting the displacement in the vertical direction of the corrected image information by reflecting the vertical movement information, to generate the road surface profile.

To be specific, the extracted image information before correcting the vertical displacement is based on respectively unique height information, and thus, the step is generated at the boundary of each extracted image, and the road travel surface cannot be precisely reproduced, but the correction based on the vertical movement information enables the step of the boundary to be eliminated and the road travel surface to be precisely reproduced.

The control panel 90 is an interface operated by the operator, etc. for performing the input necessary to operate the device in the present invention.

The display device 91 displays the screens necessary to operate the device in the present invention and the information obtained during the inspection or by the inspection.

Next, an example of how the above device is operated is explained based on FIG. 5.

At first, the vehicle in which the device is installed is positioned where the inspection of the road travel surface is started and the photographing is started (Step S 101).

The start position functions as the reference surface for specifying the inclination of the vehicle in the succeeding processing, namely of the travel surface photography means, and thus, is preferably horizontal or substantially horizontal and flat, however, any roughness of the travel surface at the starting position causes no problem, and any inclination of the travel surface at the starting position does not cause any serious problem since the inclination state is used as the reference angle of the inclination.

Next, in the basic information generation means 71, the photographic information via the travel surface photography means 21 and the information obtained by the auxiliary travel surface photography means 31 are associated by the photography timing (Step S 102), and furthermore, the movement information acquired by the movement information acquisition means 6 is associated with each information associated with the photography timing (Step S 103), and thereby, the basic information is generated (Step S 104).

It should be noted that the cycle of the photography timing and the cycle of the movement information are usually different, and thus, the interpolation calculation is performed for associating the two.

Next, in the photographic image information selection means 72, the photographic images overlapped in the predetermined range are sequentially specified and the photographic image information corresponding to the specified photographic images is selected (Step S 105).

Next, in the movement distance information generation means 73, the movement distance information of the travel surface photography means 21 in the photography timing of each selected photographic image information is generated (Step S 106).

Next, by the use of the inclination information generated in the inclination information generation means 5, in the corrected image information generation means 74, from each unit of the selected image information, the corrected image information respectively corresponding to the image information is generated (Step S 107).

Next, in the vertical movement information generation means 75, the vertical movement information relative to the travel surface photography means 21 is generated based on the difference of the positions of the light beam image included in the corrected image information (Step S 108).

Next, in the extracted image information generation means 70, the rear region and the front region included in each corrected image information are specified, and the extracted image information corresponding to the extracted region formed of the rear region and the front region are respectively generated (Step S 109).

Next, in the extracted image information connection means 76, each extracted image information is sequentially arranged and connected while the displacement in the vertical direction being corrected, based on the vertical movement information, and thereby the road surface profile is generated (Step S 110).

Next, the concept under which the processing is performed in the above Steps is explained based on FIGS. 6-10.

In the drawings, the reference numerals respectively indicate as shown below. 21-1: travel surface photography means positioned in the first position as the inspection starting point, 21-1 *a*: corrected image of travel surface photography means 21-1, 21-1 *c*: light beam image projected on the corrected image 21-1 *a*, 21-2: travel surface photography means positioned in the second position, 21-2 *a*: corrected image of travel surface photography means 21-2, 21-2 *b*: light beam image projected on the corrected image 21-2 *a*, 21-2 *b*: central axis projected on the corrected image 21-2 *a*, 21-2 *c*: light beam image projected on the corrected image 21-2 *a*, 21-3: travel surface photography means positioned in the third position, 21-3 *a*: corrected image of travel surface photography means 21-3, 21-3 *c*: light beam image projected on the corrected image 21-3 *a*, 21-4: travel surface photography means positioned in the fourth position, 21-4 *a*: corrected image of travel surface photography means 21-4, 21-4 *c*: light beam image projected on the corrected image 21-4 *a*, 21-5: travel surface photography means positioned in the fifth position, 210: difference of light beam position, L1: difference between the first position and the second position, L 2: difference between the second position and the third position, L 3: difference between the third position and the fourth position, M; locus showing the vertical movement state of the travel surface photography means 21.

It should be noted that in FIGS. 6-8, the travel surface is shown as flat for the purpose of simplifying the explanation.

Also, the angle of the travel surface photography means in FIG. 6 is set as constant, since it is shown on the basis of the corrected image.

When the photographing is started in Step S 101, the travel surface photography means 21 moves according to the travel surface photography means 21-1~21-4 shown in FIG. 6.

At this moment, the travel surface photography means 21 at each position photographies the photographic images. These positions correspond to the photographic image information selected by the photographic image information selection means 72.

The selection of the photographic image information selection in Step 105 is explained.

For example, the photographing by the light section method is performed with 10 ms (100 Hz), the travel surface photography means 21 moves by 21.0-29.3 cm with the vehicle travel speed of about 30 km/h (8.3 cm/s) and 21.0-25.1 cm with the vehicle travel speed of about 15 km/h (4.1 cm/s).

Therefore, the photographic images are set to be selected so that, as a next photographic image, a photographic image which is photographied when the movement distance exceeds 21 cm from the previous photographic image is selected.

The generation of the vertical movement information in Step 108 is explained.

It should be noted that the angle of each corrected image in FIG. 6 is already corrected.

FIG. 7 is obtained by overlapping the corrected image 21-1 *a* and the corrected image 21-2 *b* based on the movement distance information.

In this case, the difference of position 210 is generated between one light beam image of 21-1 *c* and the other light beam image of 21-2 *c*.

The difference of position 210 constitutes the relative height displacement of the travel surface photography means 21-2 to the travel surface photography means 21-1.

And, the vertical movement information is generated by sequentially calculating the relative displacement amount of each light beam image of the corrected image corresponding to the neighboring travel surface photography means.

The locus M is obtained by specifically depicting the vertical movement on the drawing.

For example, in the case of the camera of the travel surface photography means 21 having the height of 40 cm, if the length of the obtained corrected image along the travel direction is 35 cm, the obtained resolution (mm/pixel) is 35 cm/512=0.68 mm.

In this case, as the overlapped length, the movement distance of the travel surface photography means is adopted, and the obtained length is, for example, 35−(21.0~29.3) cm in the case of the speed of 30 km/h (8.3 cm/s) and 35−(21.0~25.1) cm in the case of the speed of 15 km/h (4.1 cm/s).

The generation of the corrected image in Step 109 is explained.

From the corrected image 21-2 *a* in FIG. 6, L1/2 is set as the rear region of the central axis 21-2 *b*, and L 2/2 is set as the front region.

Then, FIG. 8 is obtained by extracting the corrected region formed of the rear region and the front region from the corrected images 21-2 *b*~21-4 *b*, and sequentially arranging the corrected image information 21-2 *d*~21-4 *d* corresponding to each extracted region, while correcting the displacement in the vertical direction by the vertical movement information.

FIG. 9 shows the relation between the movement distance and the extracted region when the travel surface has ups and downs or unevenness.

Accordingly, in the Embodiment 1 in the present invention, the inclination angle of the vehicle and the travel surface photography means can be specified from the height obtained by the light section method in the travel surface photography means and the auxiliary travel surface photography means regardless of the travel speed, acceleration/deceleration, or temporal stoppages of the vehicle, the distortion of the images can be appropriately corrected, the height of the travel surface photography means can be precisely specified from the corrected images, and furthermore, the extracted regions extracted from the corrected images can be specified according to the travel state of the vehicle, thereby the road surface profile in which the road surface state of the travel road actually travelled is faithfully reproduced can be generated.

It should be noted that in the above Embodiment, the travel surface illumination means, the travel surface photography means, the auxiliary travel surface illumination means, and the auxiliary travel surface photography means may be directly installed respectively to the predetermined positions in the vehicle instead of being provided as the light section unit.

Also, in the above Embodiment, it is arranged so that the images used for generating the profile are photographied in the rear light section unit, but it may be arranged so that the images used for generating the profile are photographied in the front light section unit.

The design can be freely changed regarding where the light section unit and the auxiliary light section unit are installed with what distance between the two.

Also, in addition to the auxiliary light section unit in the above Embodiment, another auxiliary light section unit may be further provided for being capable of performing photographing along the axis different from the travel surface photography axis in the light section unit so that the inclination of the travel surface photography means can be corrected in the horizontal direction as well, in addition to the vertical direction.

Furthermore, the present invention is adaptable to any design changes within the scope of the present invention and is not limited to the above Embodiment.

Embodiment 2

Next, Embodiment 2 is explained.

Since Embodiment 2 is basically configured similarly to Embodiment 1, the difference from Embodiment 1 is mainly explained, and the overlapped explanation is omitted.

Figure 10:
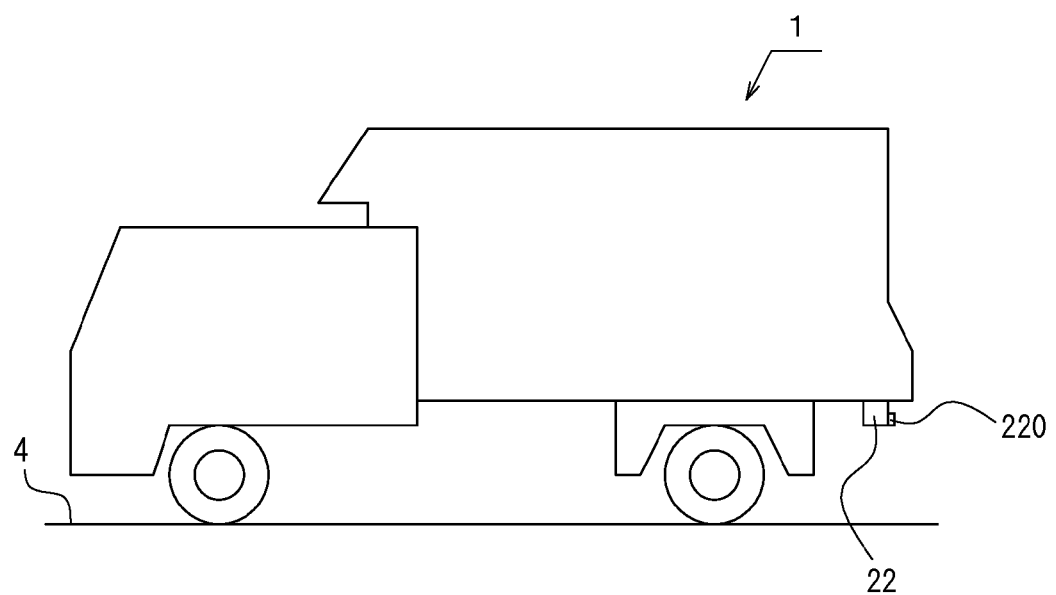
FIG. 10 is a conceptual diagram showing Embodiment 2 of the vehicle mounted with the device for inspecting the shape of the road travel surface in the present invention.
Figure 11:
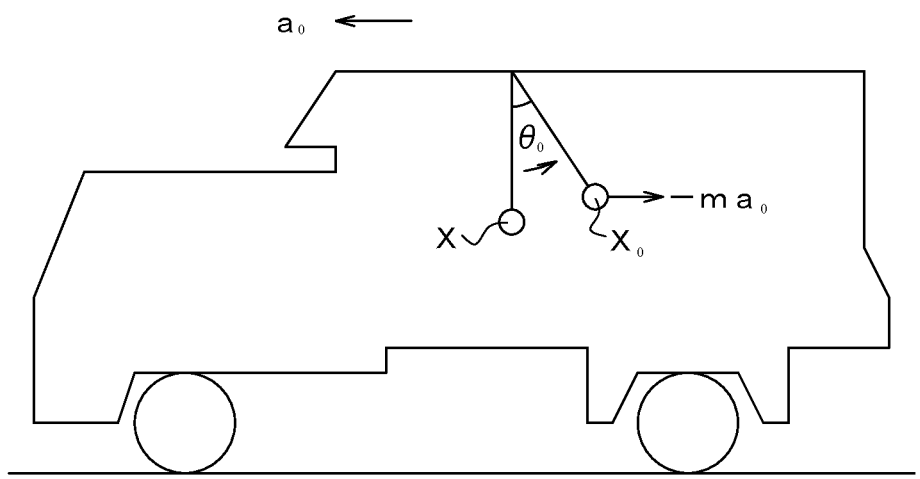
FIG. 11 is an explanation drawing for showing the correction in the gyro instrument.

FIG. 10 is a conceptual diagram showing the vehicle mounted with the device for inspecting the shape of the road travel surface in the present invention in Embodiment 2, and FIG. 11 is an explanation drawing for showing the correction in the gyro instrument.

In the drawings, reference numerals 1, 22 and 220 respectively indicate the vehicle, the light section unit, and the gyro instrument.

In this embodiment, the inclination angle of the not-shown travel surface photography means in the light section unit 22 is specified by the gyro instrument 220.

This gyro instrument 220 is dubbed gyro scope or gyro sensor, for example.

It should be noted that in such a gyro instrument 220, the acceleration/deceleration of the vehicle 1 causes measurement errors, and thus, the influence of the acceleration/deceleration is removed from the result of the inclination angle obtained from the gyro instrument 220 by additionally providing a not-shown accelerometer and correcting the inclination angle obtained from the gyro instrument 220 by the acceleration of the vehicle 1 measured by the accelerometer.

And, the photographic images are corrected according to the corrected inclination angle.

The principle of this correction is explained below on the basis of FIG. 11.

The acceleration $a_0$ generated by the acceleration of the vehicle acts the inertia force $-ma_0$ to the spindle X suspended to the vehicle.

The spindle $X_0$ on which the inertia force $-ma_0$ is acting is jerked to the side opposite the travel direction and balanced at the angle $\theta_0$.

The angle $\theta_0$ acts on the measurement result of the gyro instrument 220 and generates the measurement error.

Therefore, in the present Embodiment, the measurement result obtained in the gyro instrument 220 is corrected by the inertia force $-ma_0$ and the error caused by the angle $\theta_0$ is corrected so as to return the spindle displaced to the position of the spindle $X_0$ by the inertia force $-ma_0$ to the position of the spindle X.

In this Embodiment, the measurement error of the inclination angle can be corrected even when the gyro instrument is used and the corrected images can be appropriately overlapped. This overlapping enables the height of the travel surface photography means to be specified and the height information to be generated, and thus, the road surface profile approximate to the shape and length of the actual travel surface to be generated.

Please note the processing steps in this embodiment are similar to the processing steps in FIG. 5.

In this Embodiment 2, only one set of the light section unit is sufficient, and thus, fewer processing steps are necessary to generate the road surface profile and compactification of the facilities and the cost restraint can be advantageously achieved.

Besides, specifying the inclination angle by using the gyro instrument with quick response speed and high precision enables the high-precision road surface profile to be generated.

INDUSTRIAL APPLICABILITY

In the present invention, the vertical section profile information capable of highly reproducing the travel surface can be acquired without being influenced by the speed or temporal stoppages of the vehicle, and this profile information enables quite precise IRI analysis, thereby high level of industrial applicability is provided in terms of efficient maintenance of the road travel surface and the unified index operation.

DESCRIPTION OF THE REFERENCE NUMERALS

1 Vehicle mounted with Embodiment 1 of the device for inspecting the shape of the road travel surface in the present invention
2 Light section unit
20 Travel surface illumination means
21 Travel surface photography means
21 *a* Photography range
21 *b* Central axis
21-1 Travel surface photography means
21-1 *a* Corrected image
21-1 *c* Light beam image
21-2 Travel surface photography means
21-2 *a* Corrected image
21-2 *b* Light beam image
21-2 *b* Central axis
21-2 *c* Light beam image
21-3 Travel surface photography means
21-3 *a* Corrected image
21-3 *c* Light beam image
21-4 Travel surface photography means
21-4 *a* Corrected image
21-4 *c* Light beam image
21-5 Travel surface photography means
210 Difference of light beam position
22 Light section unit
220 Gyro device
3 Auxiliary light section unit
4 Road travel surface
40 Travel surface photography axis
41 Travel direction
8 Control means
3 Auxiliary light section unit
30 Auxiliary travel surface illumination means
31 Auxiliary travel surface photography means
5 Inclination information generation means
6 Movement information acquisition means
7 Road surface profile generation means
70 Extracted image information generation means
71 Basic information generation means
72 Photographic image information selection means
73 Movement distance information generation means
74 Corrected image information generation means
75 Vertical movement information generation means
76 Extracted image information connection means
90 Control panel
91 Display device
L 1 Distance between first position and second position
L 2 Distance between second position and third position
L 3 Distance between second position and third position
M Locus showing the vertical movement state

The invention claimed is:

1. A device installed in a vehicle, for photographing road travel surface while the vehicle travels and inspecting a shape of the road travel surface based on photographic information obtained by the photographing, comprising travel surface illumination means for emitting a light beam to the road travel surface along a travel surface photography axis set parallel to a travel direction of the vehicle, travel surface photography means installed in the vehicle at a predetermined reference angle for acquiring information necessary for a light section method by sequentially photographing from an oblique direction, with a predetermined photography range set as a unit, the travel surface photography axis in regions to which the light beam is emitted by the travel surface illumination means as a plurality of units of photography ranges of photographic images, and acquiring photographic image information, inclination information generation means for acquiring inclination information which shows inclination state of the travel surface photography means, movement information acquisition means for acquiring travel distance information of the vehicle, and road surface profile generation means for generating a road surface profile by generating corrected image information in which a tilt in the photographic image information has been corrected by using the inclination information, on the basis of the photographic imager information, the inclination information, and the movement information, then arranging the corrected image information by using the movement information, specifying vertical movement information pertaining to the travel surface photography means from image contents of overlapped regions, generating extracted image information by partially cutting out the corrected image information and, while correcting height of the corrected image by using the vertical movement information from the corrected image information, sequentially arranging and connecting the extracted image information.

2. The device claimed in claim 1 for inspecting the shape of the road travel surface, characterized in that the road surface profile generation means comprises extracted image information generation means for segmenting the photographic image to be cut out into a front region and a rear region in the travel direction on the basis of a central axis orthogonal to a travel surface reference axis, as the rear region, in a series of photographic processes, setting a width corresponding to a length which is half a movement distance specified based on the travel distance information is set, the travel distance information being to the photography position of the photographic image to be cut out from the photographic image initially photographed in a case where no photographic image has been cut out among the photographic images photographed prior to the photographic image to be cut out, and from the photography position of the photographic image which has been cut out immediately before the photographic image to be cut out in a case where any photographic images have been cut out among the photographic images photographed prior to the photographic image to be cut out, as the front region, setting a width corresponding to the length which is half the movement distance specified based on the travel distance information from the photography position of the photographic image to be cut out to the photography position of the photographic image to be cut out immediately after the photographic image to be cut out, and generating the extracted image information by cutting out an extracted region formed of the front region and the rear region sandwiching the central axis of the photographic image to be cut out.

3. The device claimed in claim 2 for inspecting the shape of the road travel surface, wherein the road surface profile generation means further comprises basic information generation means for generating basic information in which all photographic image information and movement distance information at photography timing of each photographic image information are associated, photographic image information selection means for specifying from the basic information relative position of the photographic image generated by the photographic image information in each unit, sequentially specifying, in the photographic images in each unit, the photographic images in which an edge region of the travel surface photography axis included in each photographic image overlaps the edge region of the other photographic image within a predetermined range, and selecting the photographic image information corresponding to the specified photographic images, movement distance information generation means for generating movement distance information of the travel surface photography means at the photography timing of the each selected photographic image, based on the movement distance information associated with the selected photographic image information, corrected image information generation means for generating the corrected image information in the units respectively corresponding to the selected image information in each unit by correcting the selected photography image information into the corrected image information photographed from a predetermined and specific angle by the use of the inclination information of the travel surface photography means associated with the photographic image information, the vertical movement information generation means for generating the relative vertical movement information of the cameras by comparing the overlapped regions of the images included in the neighboring corrected image information in the corrected image information in each unit, calculating the relative height displacement of cameras which have photographed the corrected image information from the distance of the positions of the light beam image included in the corrected image information, and the extracted image information connection means for generating the road surface profile by sequentially arranging and connecting each extracted image information while reflecting the vertical movement information and correcting the displacement in the vertical direction, the extracted image information generation means generating the extracted image information from the corrected images generated from the corrected image information corrected by the corrected image information generation means.

4. The device claimed in claim 1 for inspecting the shape of the road travel surface, wherein the travel surface photography means measures the height of the travel surface photography means to the road travel surface in addition to photographing the road travel surface, the travel surface photography means comprising auxiliary travel surface illumination means for emitting the light beam to the road travel surface along a travel surface auxiliary photography axis set parallel to the travel direction of the vehicle, and auxiliary travel surface photography means installed in the vehicle at the predetermined reference angle, for acquiring auxiliary photographic image information by sequentially photographing the travel surface auxiliary photography axis in the region where the auxiliary travel surface illumination means emits the light beam, from the oblique direction to the road travel surface with the predetermined photography range set as a unit while synchronizing the auxiliary photographic images in the plurality of units of photography ranges with the photography timing of the travel surface photography means, and acquiring information necessary for light section means from the road travel surface at the photography timing of the auxiliary travel surface photography means, the auxiliary travel surface photography means at least measuring auxiliary height of auxiliary travel surface to the road travel surface, inclination information generation means using information of height of the travel surface photography means, auxiliary height of the auxiliary travel surface photography means, and the distance between the travel surface photography means and the auxiliary travel surface photography means, calculating a posture change angle between the travel surface photography means and the auxiliary travel surface photography means, generating the inclination information of the vehicle while using the posture change angle as the inclination information of the vehicle, and using the inclination information of the vehicle as the inclination information of the travel surface photography means.

5. The device claimed in claim 4 for inspecting the shape of the road travel surface, wherein, a posture change angle $\theta$ is obtained by the formula shown below in a case where, among the photographic images selected by the photographic image information selection means, two sequential photographic images include an identical reference point P 1, and, in the two photographic images, height of the travel surface photography means of an antecedently photographed photographic image is defined as H 1, and height of the travel surface photography means of a subsequently photographed photographic image is defined as H 1', two sequential auxiliary photographic images photographed in synchronization with the photography timing of the photographic images photographed by the auxiliary travel surface photography means and selected by the photographic image information selection means include an identical reference point P 2 and, in the two auxiliary photographic images, auxiliary height of auxiliary travel surface photography means of an antecedently photographed auxiliary photographic image is defined as H 2, and auxiliary height of the auxiliary travel surface photography means of a subsequently photographed auxiliary photographic image is defined as H 2', and distance between the travel surface photography means and the auxiliary travel surface photography means is defined as L.

$$\text{posture change angle } \theta = \text{Atan} \frac{(H1' - H2') - (H1 - H2)}{L} \quad \text{[Formula 1]}$$

6. The device claimed in claim 1 for inspecting the shape of the road travel surface, wherein the inclination information generation means is a gyro system, and the road surface profile generation means further comprises the basic information generation means for specifying, for all the photographic image information, the inclination information at the photography timing of the photographic image information, specifying movement information corresponding to the photography timing and generating the basic information in which the inclination information and the movement information are associated with the photographic image information, the photographic image information selection means for calculating from the association of the photographic image information and the movement information the relative position of the photographic image generated by the photographic image information in each unit, sequentially specifying the photographic images in which the edge region of the travel surface photography axis included in each photographic image overlaps the edge region of the other photographic image within the predetermined range, and selecting the photographic image information generating the specified photographic images, the movement distance information generation means for generating the movement distance information of the cameras at the photography timing of each photographic image, based on the movement distance information associated with selected photographic image information, the corrected image information generation means for generating the corrected image information in the units respectively corresponding to the selected image information in each unit, by correcting the selected photography image information into the corrected image information photographed from the reference angle based on the angle information of the cameras associated with the photography image information by the use of relative photography angle information on the basis of the reference angle of the cameras, the vertical movement information generation means for generating the relative vertical movement information of the cameras by comparing the overlapped regions of the images included in the neighboring corrected image information in the corrected image information in each unit, calculating the relative height displacement of cameras which have photographed the corrected image information from the distance of the positions of the light beam image included in the corrected image information, and the extracted image information connection means for generating the road surface profile by sequentially arranging and connecting each extracted image information while reflecting the vertical movement information and correcting the displacement in the vertical direction.

\* \* \* \* \*